(12) United States Patent
Babin

(10) Patent No.: US 7,508,999 B2
(45) Date of Patent: Mar. 24, 2009

(54) FIBER OPTIC SENSOR DEVICE FOR MEASURING CHROMOPHORIC COMPOUNDS IN BIOLOGICAL FLUID

(75) Inventor: Steven M. Babin, Greenbelt, MD (US)

(73) Assignee: Johns Hopkins University, Baltimore, MD (US)

( * ) Notice: Subject to any disclaimer, the term of this patent is extended or adjusted under 35 U.S.C. 154(b) by 12 days.

(21) Appl. No.: 12/039,221

(22) Filed: Feb. 28, 2008

(65) Prior Publication Data

US 2008/0212918 A1    Sep. 4, 2008

Related U.S. Application Data

(60) Provisional application No. 60/892,588, filed on Mar. 2, 2007.

(51) Int. Cl.
*G02B 6/00* (2006.01)
(52) U.S. Cl. .............................. 385/12; 385/13; 385/53; 385/88
(58) Field of Classification Search .................. 385/12, 385/13, 53, 88
See application file for complete search history.

(56) References Cited

U.S. PATENT DOCUMENTS 5,353,790 A    10/1994    Jacques et al.
5,600,433 A *   2/1997    Buttry et al. ................ 356/128

OTHER PUBLICATIONS

Babin, Steven M., "An Experimental Study of a Coiled Unclad Fiber Optic pH Sensor", Aug. 1983, Univ. of PA, The Moore School of Engineering and Applied Science, Phil., PA, Master's Thesis.
Wolfe, Carolyn, "Feasibility Study of Distributed Feedback pH Sensors", Aug. 1979, Univ. of PA, College of Engineering and Applied Science, Phil., PA, Master's Thesis.
Zemel, J. N., Keramari, B., and Spivak, C. W., D'Amico, A., "Non-FET Chemical Sensors", Elsevier Sequoia S A, Lausanne—printed in the Netherlands, pp. 427-473, Sensors and Actuators, 1(1981).
Jacques, Steven L., Saidi, Iyad, Ladner, Anne, Oelberg, David, "Developing an Optical Fiber Reflectance Spectrometer to Monitor Bilirubinemia in Neonates" SPIE vol. 2975, pp. 115-124 1997.

* cited by examiner

*Primary Examiner*—Jennifer Doan
(74) *Attorney, Agent, or Firm*—Francis A. Cooch

(57) ABSTRACT

A fiber optic sensor device for detecting the presence of a chromophoric compound in a biological fluid is disclosed. The fiber optic sensor device includes at least one fiber optic member having an unclad portion, the fiber optic member having a proximal end and a distal end for transmitting light energy of a determinable wavelength, a light source means for generating light energy of determinable wavelength, said light source means operatively associated with a measuring means such that said light energy passes through said measuring means and said fiber optic member to the biological fluid, and measuring means operatively associated with said fiber optic member and said light source, for measuring the difference between said light energy generated by said light source and light reflected from the distal end of the fiber optic member, wherein the difference is related to the light absorbed by the chromophoric compound and indicative of the concentration of the chromophoric compound present in the biological fluid.

20 Claims, 3 Drawing Sheets

FIBER OPTIC SENSOR DEVICE FOR MEASURING CHROMOPHORIC COMPOUNDS IN BIOLOGICAL FLUID

CROSS-REFERENCE TO RELATED APPLICATIONS

This application claims the benefit of prior filed co-pending U.S. Provisional Application No. 60/892,588, filed Mar. 2, 2007, and entitled "UNCLAD FIBER OPTIC SENSOR FOR MEASURING CHROMOPHORIC COMPOUNDS IN HUMAN BLOOD AND AMNIOTIC FLUID", the contents of which are incorporated by reference herein.

BACKGROUND OF THE INVENTION

1. Field of the Invention

The present invention generally relates to a fiber optic sensor device for measuring chromophoric compounds in biological fluid such as blood, saliva, sweat, etc.

2. Description of the Related Art

Approximately 60% of infants born in the United States each year become clinically jaundiced. Jaundice, or hyperbilirubinemia, results from increased production and transiently impaired elimination of bilirubin. While most affected neonates recover rapidly, some infants show persistently high levels of unconjugated bilirubin. The potential harms associated with moderate to severe jaundice include sensorineural hearing loss, bilirubin encephalopathy and kernicterus. Kernicterus is the most dreaded consequence of hyperbilirubinemia. When it occurs, it results in, for example, irreversible brain damage, choreoathetoid cerebral palsy, mental retardation, deafness, gaze paresis, and even death. Kernicterus survivors require lifetime care, at costs estimated to be about $22 to $40 million per child. If detected early, especially in high-risk cases, hyperbilirubinemia can be treated before kernicterus or less severe disorders develop. Some of the root causes of kernicterus cited by the American Academy of Pediatrics Subcommittee on Neonatal Hyperbilirubinemia include underestimating the severity of jaundice and delay in measurement.

Presently, there are two primary methods of measuring levels of bilirubin—serum blood tests and transcutaneous readings. Serum blood tests involve infant heel pricks while skin readings are a non-invasive method useful in low risk cases. Skin bilirubin levels are related to blood levels (i.e., the higher the blood level, the higher the skin level), but they may be difficult for the physician to assess visually with accuracy (perhaps the most common cause of underestimating the severity of jaundice). Additionally, there is a time lag between the real concentration in the blood and the coloration effect on the skin and the relationship is not linear. Therefore, skin tests are not ideal to monitor more severe cases where early detection increases the chance the infant will avoid irreversible consequences. Accordingly, there remains a need for an improved method and device for high-risk patients that allows for continuous, minimally invasive, real-time monitoring of bilirubin levels in either blood or amniotic fluid.

Status asthmaticus is a life threatening medical emergency in which asthma symptoms are not responsive to standard bronchodilator therapy. The prevalence of asthma has increased about 60% among all age groups over the last two decades. As of 2005, 0.5% to 2% of children with asthma were admitted to intensive care with status asthmaticus. However, asthma-related mortality has increased at an alarming rate (e.g., from 1993-1995, the overall annual age-adjusted death rate from asthma increased 40%). Treatment options for status asthmaticus remain limited and these patients are at risk for respiratory failure and mechanical ventilation. Once admitted to a hospital, patients with acute severe asthma are often treated with an intravenous infusion of theophylline. The therapeutic range for theophylline is 10 to 20 mg/l, but side effects begin to appear above 15 mg/l. Patients may already be taking oral theophylline, in which case the blood levels will not be known in advance of emergency treatment. The usefulness of theophylline is limited by its toxic effects, including neurotoxicity (e.g., seizures) and cardiac toxicity (e.g., dysrhythmias), that have adverse consequences for the patient, including death. There is no specific treatment for these toxic effects. Therefore, one must balance the life-saving efforts of the therapy with its possible toxic consequences. Accordingly, there remains a need for an improved method and device for measuring and continuously monitoring theophylline levels during therapy for a patient suffering from severe asthma such as status asthmaticus.

SUMMARY OF THE INVENTION

In accordance with a first embodiment of present invention, a fiber optic sensor device for detecting the presence of a chromophoric compound in a biological fluid is provided comprising:

at least one fiber optic member having an unclad portion, the fiber optic member having a proximal end and a distal end for transmitting light energy of a determinable wavelength, a light source means for generating light energy of determinable wavelength, said light source means operatively associated with a measuring means such that said light energy passes through said measuring means and said fiber optic member to the biological fluid, and measuring means operatively associated with said fiber optic member and said light source, for measuring the difference between said light energy generated by said light source and light reflected from the distal end of the fiber optic member, wherein the difference is related to the light absorbed by the chromophoric compound and indicative of the concentration of the chromophoric compound present in the biological fluid.

In accordance with a second embodiment of present invention, a method for detecting the presence of a chromophoric compound in a biological fluid in a subject is provided comprising the steps of:

(a) providing a fiber optic sensor device comprising:

at least one fiber optic member having an unclad portion, the fiber optic member having a proximal end and a distal end for transmitting light energy of a determinable wavelength, a light source means for generating light energy of determinable wavelength, said light source means operatively associated with a measuring means such that said light energy passes through said measuring means and said fiber optic member to the biological fluid, and measuring means operatively associated with said fiber optic member and said light source, for measuring the difference between said light energy generated by said light source and light reflected from the distal end of the fiber optic member, said reflected light being related to the light absorbed by the chromophoric compound;

(b) exposing the fiber optic member having an unclad portion of the fiber optic sensor device to an environment containing the biological fluid, and (c) measuring the difference between said light energy generated by said light source of the fiber optic sensor device and the light reflected from the distal end of the fiber optic member, said measurement being indicative of the concentration of the chromophoric compound present in the biological fluid.

The term "subject" or "a patient" or "a host" as used herein refers to mammalian animals, preferably human.

BRIEF DESCRIPTION OF THE DRAWINGS

Other objects, features and advantages of the present invention will occur to those skilled in the art from the following description of preferred embodiments and the accompanying drawings, in which.

DETAILED DESCRIPTION OF THE PREFERRED EMBODIMENTS

The present invention provides a fiber optic sensor device for detecting the presence of a chromophoric compound in a biological fluid. Chromophoric compounds to be detected by the fiber optic sensor device and methods of the present invention include, but are not limited to, bilirubin, theophylline, cortisol and the like. The biological fluids herein include, but are not limited to, blood, saliva, sweat, amniotic fluid, urine, tears and the like.

Figure 1A:
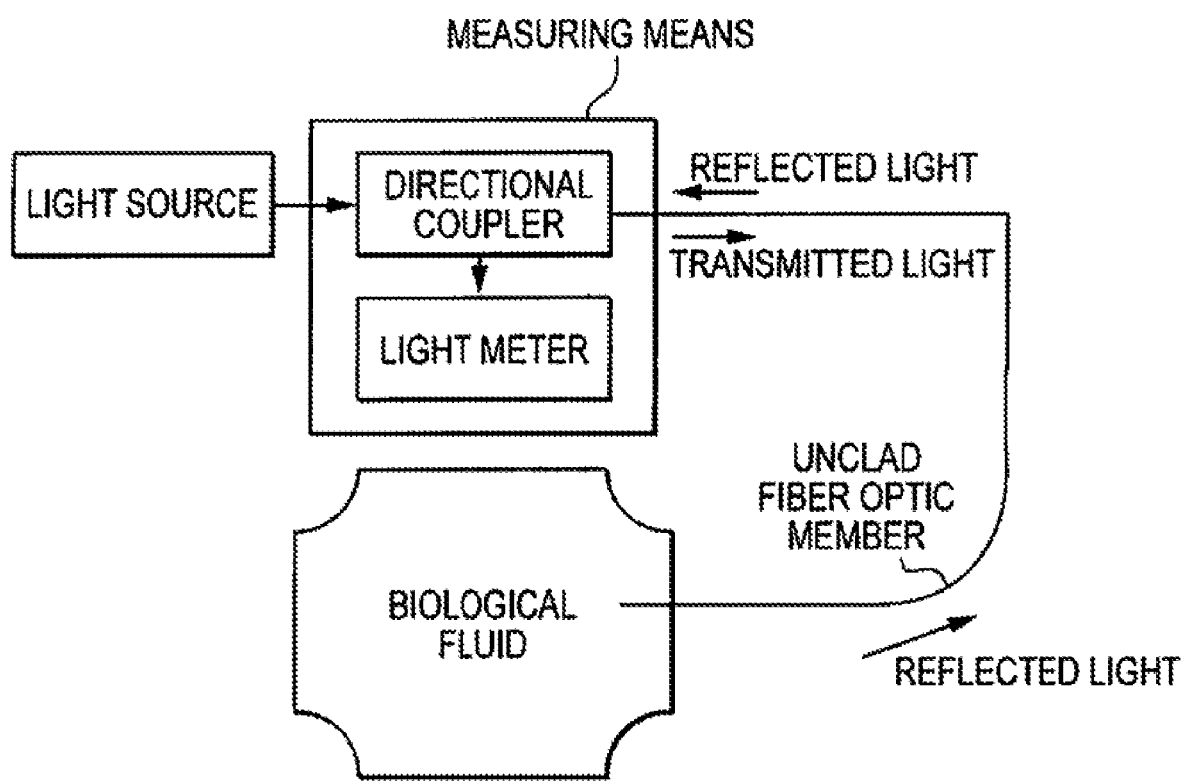
FIG. 1a is a schematic drawing of a fiber optic sensor device in accordance with one embodiment of the present invention.

In one embodiment, a fiber optic sensor device is a multi mode sensor device for detecting the presence of a chromophoric compound in a biological fluid and is generally depicted in FIG. 1a and includes:

at least one fiber optic member having an unclad portion, the fiber optic member having a proximal end and a distal end for transmitting light energy of a determinable wavelength, a light source means for generating light energy of determinable wavelength, said light source means operatively associated with a measuring means such that said light energy passes through said measuring means and said fiber optic member to the biological fluid, and measuring means operatively associated with said fiber optic member and said light source, for measuring the difference between said light energy generated by said light source and light reflected from the distal end of the fiber optic member, wherein the difference is related to the light absorbed by the chromophoric compound and indicative of the concentration of the chromophoric compound present in the biological fluid.

Figure 1B:
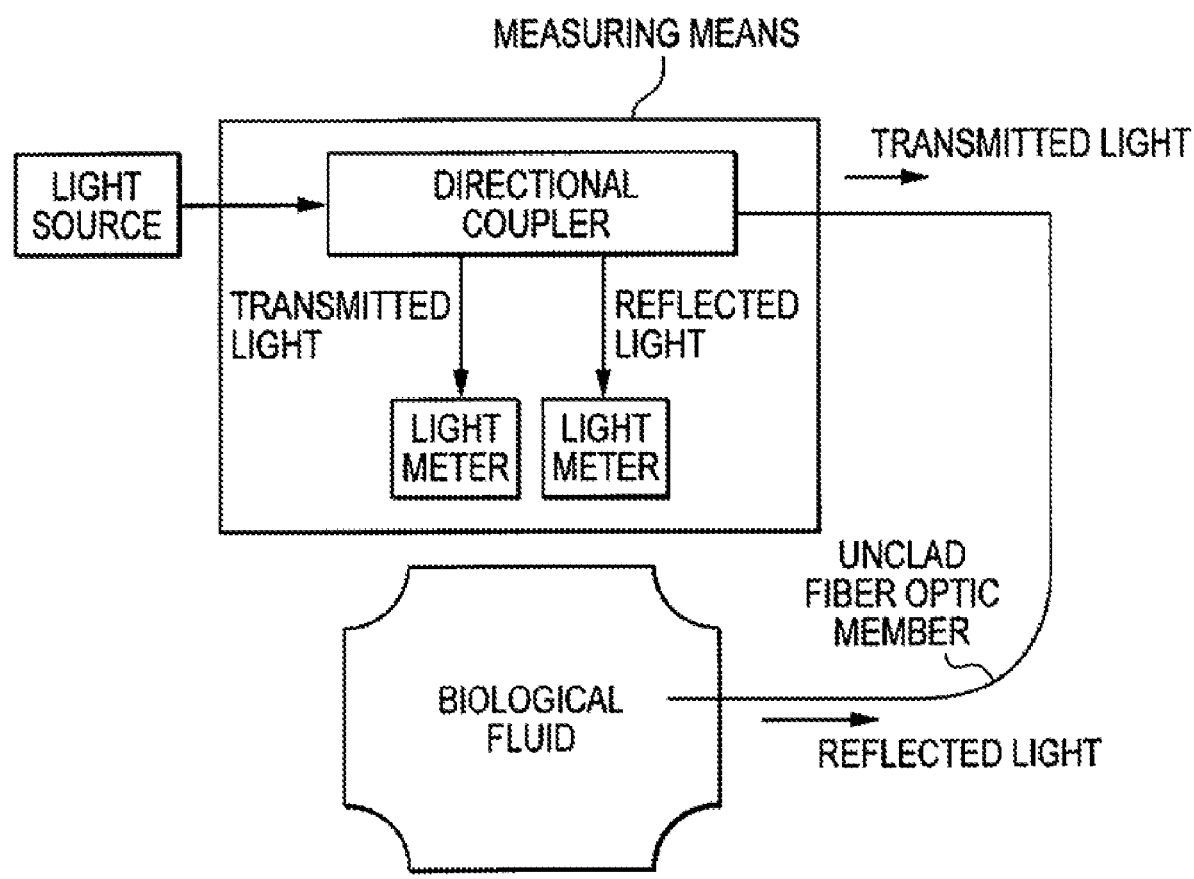
FIG. 1b is a schematic drawing of a fiber optic sensor device in accordance with one embodiment of the present invention.
Figure 2:
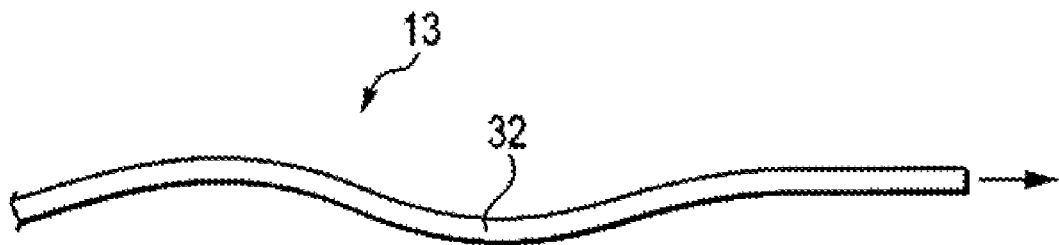
FIG. 2 is a cross-sectional view, enlarged for purposes of clarity, of an unclad fiber optic for use in the fiber optic sensor device of FIGS. 1a and 1b.
Figure 3:
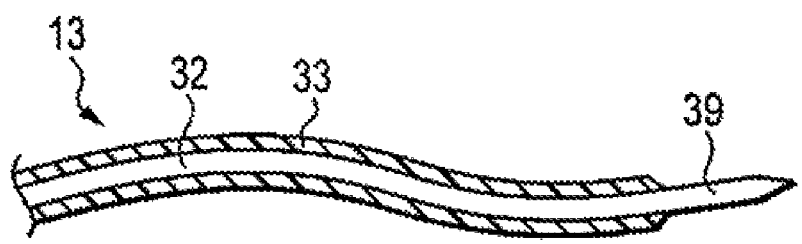
FIG. 3 is a cross-sectional view, enlarged for purposes of clarity, of an alternative embodiment of an unclad fiber optic and clad fiber optic for use in the fiber optic sensor device of FIGS. 1a and 1b.

Referring now to FIGS. 2 and 3, there are shown details of a fiber optic member 13. Generally speaking, as shown in FIG. 2, fiber optic member 13 is unclad and includes a core 32. As to its optical properties, core 32 of fiber optic member 13 should be formed of a material which transmits light without substantial attenuation in the wavelengths that provide the most meaningful signal information to the measuring means of FIGS. 1a and 1b. As to its physical properties, core 32 of fiber optic member 13 should be formed of a material that is capable of being inserted into the body of a subject. Suitable core material for core 32 of unclad fiber optic member 13 include polymeric material such as polymethyl methacrylate, polyvinyl chloride, and the like; glass such as chalcogenide glass, and the like. Suitable chalcogenide glass fibers can be commercially obtained from various sources. Unclad fiber member 13 can be obtained by commercially available sources as Polymicro Technology (Phoenix, Ariz.) or as described below with respect to the embodiment depicted in FIG. 3.

In one embodiment, fiber optic member 13 can also include a core 32 and a thin cladding 33 which forms a sheath around the core as generally depicted in FIG. 3 for use in the fiber optic sensor device of FIGS. 1a and 1b (not shown). The cladding 33 has the purpose of preventing light from entering or leaving the sides of the core. Although various cladding materials can be used, the most suitable ones have refractive indices which provide high total internal reflection of light at the cladding-core interface. This requirement can also be stated conversely by saying that the preferred cladding materials do not provide strong internal absorption of light. Optical fibers having a core 32 and a thin cladding are well known in the art.

In the embodiment illustrated in FIG. 3, cladding 33 extends the entire length of core 32 except for an unclad section 39 where core 32 of unclad section 39. Typically, the diameter of unclad section 39 ranges from about fifty to about three hundred microns. It is preferred that the unclad section 39 be at the distal end of fiber optic member 13. Generally, at least the unclad section 39 of fiber optic member 13 should be nontoxic and acceptable for use in a subject. The term "nontoxic" and "acceptable" as used herein shall be understood in a relative sense and is intended to designate any material that has been approved by the United States Food and Drug Administration ("FDA") for insertion into a subject such as a human or, in keeping with established regulatory criteria and practice, is susceptible to approval by the FDA for administration to humans. In practice, unclad section 39 can be formed either by removing cladding 33 from core 32 or by fusing an unclad core section to optical fiber. As to the latter alternative, it should be understood that the remainder of the optical fiber need not be made of the same material as unclad section 39 although, in the preferred embodiment, the material of the sensor section is the same as the remainder of the optical fiber. Alternatively, a core 32 having cladding 33 can be coupled to the unclad optical fiber by way of a fiber optic coupler as known in the art.

Suitable non-limiting examples of light source means include an argon laser, blue laser, tunable laser, light emitting diode (LED), and the like. Preferably, the light source means is a LED.

Measuring means for measuring absorption (i.e., the difference between the transmitted light entering the fiber optic member and the reflected light returning from the distal end of the fiber optic member), include a directional coupler, available from such sources as Fiber Optic Network Technology Co. (Surrey, British Columbia, Canada) and the like, operatively associated with at least one light meter, such as those available from such sources as Calright Instruments (San Diego, Calif.), Reliability Direct (League City, Tex.) and Optical Wavelength Laboratories (Whitewater, Wis.). Both a directional coupler and light meter are well known in the art. The directional coupler should be a multi mode directional coupler. In one embodiment, a plurality of light meters can be used to measure absorption (see FIG. 1b).

Figure 4:
FIG. 4 is a cross-sectional view, enlarged for purposes of clarity, of an alternative embodiment of an unclad fiber optic and clad fiber optic for use in the fiber optic sensor device of FIGS. 1a and 1b.

In this embodiment, the measuring means is operatively associated with the fiber optic member and the light source. In use, the unclad section of the fiber optic member is inserted into the body of a subject via, for example, a cannula or catheter. In one embodiment, the unclad section of the fiber optic member is inserted directly into the bloodstream through a pre-existing catheter to monitor the levels of a chromophoric compound such as bilirubin or theophylline in the blood. The light source will transmit light according to the maximum absorption of the chromophoric compound into the fiber optic member which travels along the optical fiber to its distal end. Absorption will occur in the evanescent portion of the light that extends outside the unclad section of the fiber optic member in the bloodstream. As one skilled in the art will readily appreciate, the light source will transmit light according to the maximum absorption of the specific chromophoric compound being detected. For example, hemoglobin in the blood would not interfere because it absorbs at a different frequency than bilirubin and theophylline. The modified light is then reflected back using, for example, a mirror coating 40 on the end of the fiber optic member 13 as generally depicted in FIG. 4 or a bragg grating as known in the art, along the same or another fiber to the measuring means which interprets the returned light signal. Mirror coatings and techniques for applying are well known in the art and include, e.g., pyrex, aluminum, or silver coatings.

The measuring means will compare the light transmitted into the fiber optic member from the light source with the light reflected back to determine the light absorption accruing at the unclad section of the fiber optic member located in vivo (e.g., the blood). The absorption is related to the concentration of the chromophoric compound such as bilirubin in the blood. In this manner, exact measurements can be taken which indicate real-time levels. Real-time, as opposed to episodic measurement in vitro, will assist to prevent the adverse consequences of high levels of bilirubin or theophylline. For example, the device would allow for earlier and more accurate detection and better monitoring of, for example phototherapy in the case of jaundice. Phototherapy would not interfere with this monitoring so that measurement can occur simultaneously with therapy, ensuring that the exact length of treatment is achieved. This device would also reduce the risk of phototherapy resulting in overheating or eye damage. Additionally, in the case of treating asthma patients with theophylline, there would be less risk of theophylline toxicity.

In the case of monitoring the level of bilirubin in a fetus, the unclad section of the fiber optic member can be inserted into the subject such as in utero via a cannula and placed in contact with the amniotic sac. The light source will transmit light according to the maximum absorption of the bilirubin into the fiber optic member which travels along the optical fiber to its distal end. Absorption will occur in the evanescent portion of the light that extends outside the unclad section of the fiber optic member in contact with the amniotic sac. The modified light is reflected back using, for example, a mirror coating on the distal end of the fiber optic member, along the fiber to the measuring means which interprets the returned light signal. If desired, the fiber optic sensor device of the present invention can be connected to an automated control to monitor therapy. For example, because the device could be run continuously for blood monitoring, the output bilirubin measurement could be used to switch off the bili-light used for phototherapy for infants. That is, when the bilirubin levels in the blood drop below a certain predetermined value, the phototherapy light could be switched off. In the case of monitoring theophylline in the blood, automated control could be configured to determine when the level of theophylline is increased to a level having the potential for the risk of toxicity. Accordingly, when such as level is reached, the administration of theophylline could be reduced, thereby mitigating the risk of a toxic reaction in the patient while maintaining enough of a blood level to provide a therapeutic effect for treating status asthmaticus.

While the above description contains many specifics, these specifics should not be construed as limitations of the invention, but merely as exemplifications of preferred embodiments thereof. Those skilled in the art will envision many other embodiments within the scope and spirit of the invention as defined by the features and advantages appended hereto.

What is claimed is:

1. A fiber optic sensor device for detecting the presence of a chromophoric compound in a biological fluid is provided comprising:
   at least one fiber optic member having an unclad portion, the fiber optic member having a proximal end and a distal end for transmitting light energy of a determinable wavelength, the unclad portion of the fiber optic member being inserted into the body of a subject and in contact with the biological fluid,
   a light source means for generating light energy of determinable wavelength, said light source means operatively associated with a measuring means such that said light energy passes through said measuring means and said fiber optic member to the biological fluid, and
   measuring means operatively associated with said fiber optic member and said light source, for measuring the difference between said light energy generated by said light source and light reflected from the distal end of the fiber optic member, wherein the difference is related to the light absorbed by the chromophoric compound and indicative of the concentration of the chromophoric compound present in the biological fluid.

2. The fiber optic sensor device of claim 1, wherein the chromophoric compound is selected from the group consisting of bilirubin, theophylline and cortisol.

3. The fiber optic sensor device of claim 1, wherein the biological fluid is selected from the group consisting of blood, saliva, sweat, amniotic fluid, urine and tears.

4. The fiber optic sensor device of claim 1, wherein the chromophoric compound is bilirubin or theophylline and the biological fluid is blood.

5. The fiber optic sensor device of claim 1, wherein the light source means is selected from the group consisting of an argon laser, blue laser, tunable laser and light emitting diode.

6. The fiber optic sensor device of claim 1, wherein the measuring means comprises a directional coupler operatively associated with one or more light meters.

7. The fiber optic sensor device of claim 1, wherein a mirror coating is plated at the distal end of the fiber optic member.

8. The fiber optic sensor device of claim 1, wherein the fiber optic member comprises a cladded portion at the proximal end of the fiber optic member and an unclad portion at the distal end of the fiber optic member.

9. The fiber optic sensor device of claim 1, wherein interaction of the chromophoric compound with the light is interactive with an evanescent wave form of the input light.

10. A method for detecting the presence of a chromophoric compound in a biological fluid of a subject, the method comprising the steps of:
(a) providing a fiber optic sensor device comprising:
at least one fiber optic member having an unclad portion, the fiber optic member having a proximal end and a distal end for transmitting light energy of a determinable wavelength,
a light source means for generating light energy of determinable wavelength, said light source means operatively associated with a measuring means such that said light energy passes through said measuring means and said fiber optic member to the biological fluid, and
measuring means operatively associated with said fiber optic member and said light source, for measuring the difference between said light energy generated by said light source and light reflected from the distal end of the fiber optic member, said reflected light being related to the light absorbed by the chromophoric compound;
(b) exposing the fiber optic member having an unclad portion of the fiber optic sensor device to an environment containing the biological fluid, and
(c) measuring the difference between said light energy generated by said light source of the fiber optic sensor device and the light reflected from the distal end of the fiber optic member, said measurement being indicative of the concentration of the chromophoric compound present in the biological fluid.

11. The method of claim 10, wherein the chromophoric compound is selected from the group consisting of bilirubin, theophylline and cortisol.

12. The method of claim 10, wherein the biological fluid is selected from the group consisting of blood, saliva, sweat, amniotic fluid, urine and tears.

13. The method of claim 10, wherein the chromophoric compound is bilirubin or theophylline and the biological fluid is blood.

14. The method of claim 10, wherein the light source means is selected from the group consisting of an argon laser, blue laser, tunable laser, and light emitting diode.

15. The method of claim 10, wherein the measuring means comprises a directional coupler operatively associated with one or more light meters.

16. The method of claim 10, wherein a mirror coating is plated at the distal end of the fiber optic member.

17. The method of claim 10, wherein the fiber optic member comprises a cladded portion at the proximal end of the fiber optic member and an unclad portion at the distal end of the fiber optic member.

18. The method of claim 10, wherein interaction of the chromophoric compound with the light is interactive with an evanescent wave form of the input light.

19. The method of claim 10, wherein the step of exposing the fiber optic member to an environment containing the biological fluid comprises inserting the unclad portion of the fiber optic member into the bloodstream of the subject.

20. The method of claim 10, wherein the step of exposing the fiber optic member to an environment containing the biological fluid comprises contacting the amniotic sac of the subject with the unclad portion of the fiber optic member.

* * * * *